United States Patent [19]

Powell

[11] 4,219,563
[45] Aug. 26, 1980

[54] CYCLOPROPANECARBOXYLATE PESTICIDES

[75] Inventor: James E. Powell, Ripon, Calif.

[73] Assignee: Shell Oil Company, Houston, Tex.

[21] Appl. No.: 50,735

[22] Filed: Jun. 21, 1979

[51] Int. Cl.$^2$ ................. A01N 9/20; C07C 131/02
[52] U.S. Cl. ................. 424/304; 260/326 N; 260/347.4; 260/430; 260/465 D; 260/501.11; 260/544 L; 424/274; 424/285; 424/305; 424/307; 424/309; 560/35; 560/118; 560/124; 562/440; 562/500; 562/506
[58] Field of Search ............ 260/347.4, 326 N, 465 D; 560/35, 118, 124; 424/274, 285, 304, 305, 307, 309

[56] References Cited

U.S. PATENT DOCUMENTS 3,922,269  11/1975  Elliott et al. .................. 260/347.4

OTHER PUBLICATIONS

Elliott et al, J. Chem. Soc. Perkin, I, (1974) 2470–2474.

Primary Examiner—Richard Raymond

[57] ABSTRACT

Compounds of the formula

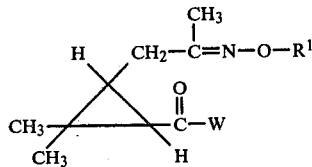

wherein $R^1$ is a hydrocarbyl group, W is a chlorine or bromine atom or —OR in which R is H, a salt-forming cation, an alkyl group or the residue of a pyrethroid alcohol are new pesticides or intermediates therefore. The compounds are prepared using a multi-step synthesis starting from the natural terpene, 3-carene.

7 Claims, No Drawings

CYCLOPROPANECARBOXYLATE PESTICIDES

BACKGROUND OF THE INVENTION

1. Field of the Invention

The present invention is directed to new cyclopropane compounds, their use in pest control and to pest control formulations containing the new cyclopropanecarboxylates.

2. Summary of the Invention

The present invention relates to new cyclopropane compounds of the formula

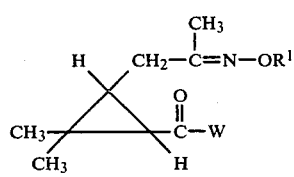

wherein $R^1$ is an alkyl group containing from 1 to 10 carbon atoms optionally substituted by one or more halogen atoms; a (cycloalkyl)alkyl group containing from 3 to 7 ring carbon atoms, a total of from 4 to 9 carbon atoms and optionally ring-substituted by one or more halogen atoms; a cycloalkyl group containing from 3 to 7 ring carbon atoms; an alkenyl group containing from 2 to 4 carbon atoms optionally substituted by one or more halogen atoms; an alkynyl group containing from 2 to 4 carbon atoms or an aryl group containing from 6 to 12 carbon atoms or an aralkyl group containing from 7 to 10 carbon atoms, each optionally ring-substituted by one or more halogen atoms; W is a chlorine or bromine atom or —OR in which R is a hydrogen atom, a salt-forming cation, an alkyl group containing from 1 to 20 carbon atoms or a group of the formula

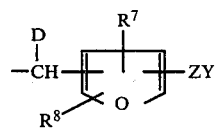  I or

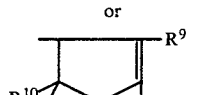  II or

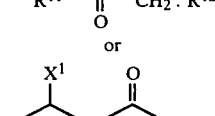  III or

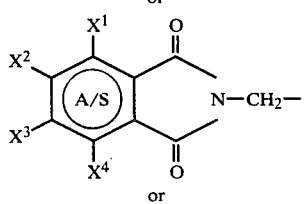  IV or

-continued

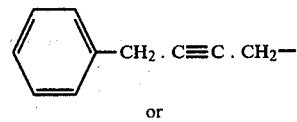  V or

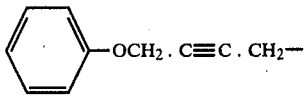  VI or

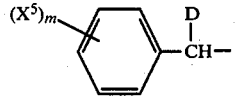  VII or

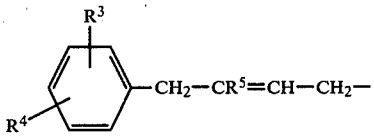  VIII or

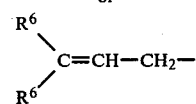  IX wherein Y represents hydrogen or an alkyl, alkenyl or alkynyl group or an aryl or furyl group which is unsubstituted or substituted in the ring by one or more alkyl, alkenyl, alkoxy or halogeno groups, $R^7$ and $R^8$, which may be the same or different, each represent hydrogen or an alkyl or alkenyl group, $R^9$ represents hydrogen or a methyl group, $R^{10}$ and $R^{11}$ represent hydrogen or an alkyl group, $R^{12}$ represents an organic radical having carbon-carbon unsaturation in a position α to the $CH_2$ group to which $R^{12}$ is attached, A/S indicates an aromatic ring or a dihydro or tetrahydro analogue thereof, $X^1$, $X^2$, $X^3$ and $X^4$, which may be the same or different, each represents hydrogen, halogen or a methyl group, D represents H, —CN, —C≡CH or

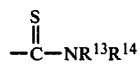

in which $R^{13}$ and $R^{14}$ may be the same or different, each represent a hydrogen atom or an alkyl group containing from 1 to 10 carbon atoms, Z represents —$CH_2$—, —O—, —CO— or —S—, $Z^1$ and $Z^2$, which may be the same or different, each represent halogen or an alkyl group containing 1 to 4 carbon atoms and n is 0, 1 or 2, $R^3$ and $R^4$ each independently is a hydrogen atom, a halogen atom having an atomic number of from 9 to 35, inclusive, an alkyl group containing from 1 to 4 carbon atoms or a nitro group, $R^5$ is a hydrogen atom or a halogen atom, each $R^6$ is a halogen atom having an atomic number of from 9 to 35, inclusive, each $X^5$ is independently a halogen atom and m is an integer of from 1 to 5, with the proviso that when D is —CN, —C≡CH or

then the alcohol moiety is in the R,S-racemic or in the S-optical configuration.

In the above formulas, suitable halogen atoms substituents are chlorine, fluorine or bromine.

The cyclopropane compounds exhibit geometrical and optical isomerism by virtue of the double bond and the two asymmetric centers in the cyclopropane ring. Consequently, the compounds can be prepared in optically active forms, which can subsequently be mixed together, or as racemic mixtures, which can subsequently be prepared as optically active forms. Because they usually provide the highest degree of pest control, the (1R,cis) esters are preferred although the (1R,trans) esters are also active. In the esters of α-substituted alcohols in which D in formulas I, IV or VII is other than hydrogen, there is a further possibility of optical isomerism, i.e., as R or as S optical configuration; the former are without practical pest control activity. In addition, optically active forms can be separated into the individual geometrical isomers.

Examples of species within the scope of the present invention include:

α-cyano-3-phenoxybenzyl 2,2-dimethyl-3-(2-(isobutoxyimino)-propyl)cyclopropanecarboxylate, 5-benzyl-3-furylmethyl 2,2-dimethyl-3-(2-(neopentoxyimino)-propyl)cyclopropanecarboxylate, α-ethynyl-3-phenoxybenzyl 2,2-dimethyl-3-(2-(cyclopropylmethoxyimino)propyl)cyclopropanecarboxylate, α-thiocarbamoyl-3-phenoxybenzyl 2,2-dimethyl-3-(2-(propargyloxyimino)propyl)cyclopropanecarboxylate.

3-benzylbenzyl 2,2-dimethyl-3-(2-(trichloroethoxyimino)-propyl)cyclopropanecarboxylate and 3-phenylthiobenzyl 2,2-dimethyl-3-(2-(p-chlorophenoxyimino)-propyl)cyclopropanecarboxylates.

Matsui et al., *Agr. Biol. Chem.*, 29, No. 8, p. 784–786, (1965) discloses the preparation of 2,2-dimethyl-3-(2-oxopropyl)cyclopropanecarboxylic acid of formula X

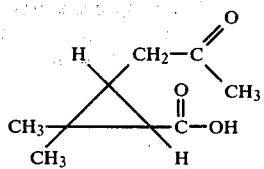

from Δ³-carene.

Treatment of an aqueous, preferably buffered, solution of this acid with hydroxylamine or a hydrocarbyloxyamine of the formula R¹NHOH or an acid addition salt thereof yields the corresponding novel oxyimino-substituted acid of the invention wherein W is OH.

The alcohols of the groups of formulas I through IX, inclusive, are known in the art, as for example in Elliott et al., U.S. Pat. Nos. 3,567,740 and 3,922,269 or Belgian Pat. Nos. 839,360 and 862,109. The pest control esters of the present invention can be prepared by esterification involving the reaction of an alcohol or derivative thereof of formula RQ, e.g., of formula XI, and a cyclopropanecarboxylic acid or derivative of formula XII

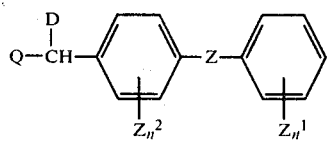

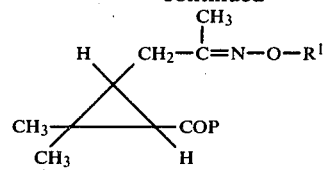

wherein Q and COP are functional groups or atoms which will react to form an ester linkage and R¹, D, Z, Z¹ and Z² are defined above.

It is usually convenient in practice either to treat the acid or acid halide with the alcohol (COP=COOH or CO-halide and Q=OH) or to treat a halogeno compound (Q=halogen) with a salt of the carboxylic acid (COP-COO-M) where M is, for example, a silver or ammonium cation.

Suitable routes to the esters in which D is

are similar to those described in Belgian patent 839,360. One route involves treating the corresponding nitrile (D is —CN) with hydrogen sulfide in the presence of a basic catalyst, preferably in the presence of a solvent. Useful solvents are lower alkanols, pyridine, or preferably a dipolar aprotic solvent such as dimethylformamide or hexamethylphosphoramide. The catalyst is preferably a strong nitrogeneous base, particularly a tertiary amine such as triethylamine, trimethylamine, or the like, or an alkanolamine, such as triethanolamine, and the like. The reaction can be carried out at room temperature. It is desirable that the reaction solution be saturated with hydrogen sulfide.

Alcohols of formula RQ where R is a group of formula IV may be prepared by reduction of the corresponding acids, esters or aldehydes, e.g., with hydride, or by conversion of the corresponding halide to an ester, e.g., by reaction with sodium acetate, followed by hydrolysis of the ester, or by reaction with formaldehyde of a Gringard reagent derived from the corresponding halide. The halides of formulas RQ where R is a group of formula IV can be prepared by halomethylation of the compound

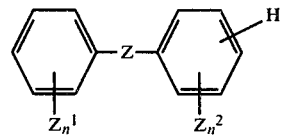

or side chain halogenation of

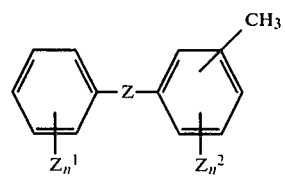

As stated earlier, the esters wherein W is OR in which R is a group of formula I–IX are useful pest control agents having the ability to knock down insects, such as houseflies, or repel mites and/or to kill insects or mites. The particular mode of pest control activity (high knockdown, repelling or killing action) can vary with the individual cyclopropanecarboxylate ester of the invention and thus depends on the specific combination of acid and alcohol moieties.

The invention includes, within its scope, pest control compositions comprising an agriculturally acceptable adjuvant—that is, at least one carrier or a surface-active agent—and, as active ingredient, at least one pest control ester of this invention. Likewise, the invention includes also a method of controlling insect, acarine or other arthropod pests at a locus which comprises applying to the pests or to the locus a pest controlling effective amount of at least one ester of the invention.

With respect to the spectrum of pesticidal activity, the compounds of this invention exhibit a selective or non-selective activity as insecticides or acaricides against one or more species of such orders as *Coleoptera, Lepidoptera*, (especially larvae), *Diptera, Orthoptera, Hemiptera, Homoptera* and *Acarina* depending upon the specific combination of acid and alcohol moieties according to the present invention. The compositions according to the present invention are useful for controlling one or more disease-carrying insects such as mosquitoes, flies and cockroaches, grain insects such as rice weevil (*Sitophilus oryzae*) and mites as well as agricultural noxious insects such as planthoppers, green rice leafhopper (*Nephotettix bipuntatus cinticeps* Uhler), diamondback moths (*Plutella maculipennis* Curtis), imported cabbage worm *Pieris rapae* Linne), rice stem borers (*Chilo suppressalis* Walker), corn earworm larvae (*Heliothis zea* Boddie), aphids, tortrixes, leaf-miners and the like.

The pesticidal esters of the invention are used for harvested crops, horticultural application, forests, cultures in green house, and packaging materials for foodstuffs, household applications and as ectoparasiticides.

The term "carrier" as used herein means a material that may be inorganic or organic and of synthetic or natural origin with which the active compound is mixed or formulated to facilitate its application to the plant, seed, soil and other object to be treated, or its storage, transport or handling. The carrier may be a solid or a liquid.

suitable solid carriers may be natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; solid polychlorophenols; bitumen, waxes such as beeswax, paraffin wax, and chlorinated mineral waxes; degradable organic solids, such as ground corn cobs and walnut shells; and solid fertilizers, for example, superphosphates.

Suitable liquid carriers include solvents for the compounds of this invention and liquids in which the toxicant is insoluble or only slightly soluble.

Examples of such solvents and liquid carriers, generally, are water, alcohols, for example, isopropyl alcohol, ketones, such as acetone, methyl ethyl ketone, methyl isobutyl ketone and cyclohexanone; ethers; aromatic hydrocarbons such as benzene, toluene and xylene; petroleum fractions, such as kerosene, light mineral oils, chlorinated hydrocarbons, such as methylene chloride, perchlorethylene, trichlorethane, including liquified, normally vaporous, gaseous compounds. Mixtures of different liquids are often suitable.

If used, the surface-active agent may be an emulsifying agent or a dispersing agent or a wetting agent. It may be nonionic, ionic or preferably, mixtures of both. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acid salts of low molecular weight, mono-, di-, and trialkylamines; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts of sulfonated castor oil, and sodium alkylarlyl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols. Encapsulated formulations and controlled release formulations are also contemplated, as are bait formulations. Wettable powders are usually compounded to contain 25, 50 or 75% w of toxicant and usually contain, in addition to solid carrier, 3–10% w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of toxicant. Granules may be manufactured by extrusion of plastics, agglomeration or impregnation techniques. Generally, granules will contain ½–25% w toxicant and 0–10% w of additives such as stabilizers, slow release modifiers and binding agents. Emulsifiable concentrates usually contain, in addition to the solvent, and when necessary, cosolvent, 10–50% w/v toxicant, 2–20% w/v emulsifiers and 0–20% w/v of appropriate additives such as stabilizers, penetrantes and corrosion inhibitors. Suspension concentrates are compounded so as to obtain a stable, nonsedimenting, flowable product and usually contain 10–75% w toxicant, 0–5% w of dispersing agents, 0.1–10% w of suspending agents such as protective colloids and thixotropic agents, 0–10% w of appropriate additives such as defoamers, corrosion inhibitors, stabilizers, penetrantes and stickers, and as carrier, water or an organic liquid in which the toxicant is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention. ingredients, for example, other compounds possessing pesticidal, herbicidal or fungicidal properties, or attractants, such as pheromones, attractive food ingredients, and the like, for use in baits and trap formulations Particularly useful compositions can be obtained by using a mixture of two or more kinds of the present compounds or by the use of synergists, such as those known for use with the general class of "pyrethroid" compounds, especially α-[2-(2-butoxyethoxy)ethoxy]-4,5-methylenedioxy-2-propyltoluene also known as piperonyl butoxide, 1,2-methylenedioxy-4-[2-(octylsulfinyl)propyl]benzene, 4-(3,4-methylenedioxyphenyl)-5-methyl-1,3-dioxane also known as safroxane, N-(2-ethyhexyl)bicyclo-[2,2,1]hept-5-ene-2,3-dicarboxamide, octachlorodipropyl ether, isobornyl thiocyanoacetate, and other synergists used for allethrin and pyrethrin. Useful compositions can be prepared with other biological chemicals including other cylopropanecarboxylates, organic phosphate-type insecticides and carbamate-type insecticides.

The compositions of the invention are applied in sufficient amount to supply the effective dosage of active ingredient at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect or acarine species to be controlled and the like, proper consideration and resolution of these factors to provide the necessary dosage of active material at the locus being within the skill of those versed in the art. In general, however, the effective dosage of active ingredient of this invention at the locus to be protected—i.e., the applied dosage—is of the order of 0.01% to 0.5% based on the total weight of the formulation, though under some circumstances the effective concentration will be as little as 0.001% or as much as 2%, on the same basis.

Illustrative Embodiments

The invention is illustrated by the following embodiments which describe the preparation of typical species of the invention. The embodiments are presented for the purpose of illustration only, and should not be regarded as limiting the invention in any way. The identity of the products, including intermediates, was confirmed by elemental, infrared and nuclear magnetic resonance spectral (NMR) analyses as necessary.

Embodiment I (1R,cis)-2,2-Dimethyl-3-(2-(isopropoxyimino)propyl)-cyclopropanecarboxylic acid To a solution of 1.85 g of sodium bicarbonate in 50 ml of water, were added 1.70 g of (1R,cis)-2,2-dimethyl-3-(2-oxopropyl)cyclopropanecarboxylic acid and 1.15 g of isopropoxyamine hydrochloride at room temperature. The reaction mixture was stirred at room temperature for 4.5 hours and filtered through celite. The filtrate was acidified with concentrated hydrochloric acid to a pH of 2, and extracted with methylene chloride. The organic extract was washed with a sodium chloride solution, dried over magnesium sulfate, stripped and concentrated under high vacuum to give the desired product as a slightly amber oil.

Embodiment II

α-Cyano-3-phenoxybenzyl (1R,cis)-2,2-dimethyl-3-(-2-(isopropoxyimino)propyl)-cyclopropanecarboxylate To a stirred solution of 0.456 g of potassium carbonate and 0.005 g of benzyltriethylammonium chloride in 6 ml of water, was added 1.5 g of (1R,cis)-2,2-dimethyl-3-(2-(isopropoxyimino)propyl)cyclopropanecarboxylic acid, prepared as in Embodiment I above, in 10 ml of toluene, and subsequently 1.9 g of α-cyano-3-phenoxybenzyl bromide. The resulting reaction mixture was stirred and heated at 65° C. for 2 hours. The reaction mixture was then allowed to cool and settle for 2 days. The toluene phase was separated, washed succesively with 25 ml of water, 10 ml of saturated sodium bicarbonate, and 10 ml of saturated sodium chloride solutions, dried over magnesium sulfate and stripped under high vacuum to give 2.8 g of a yellow oil. The oil was absorbed on silica gel and chromatographed using a mixture of pentane/ether (4:1) as the eluent to yield (a) 1.0 g of the desired product as a higher Rf isomer mixture and (b) 0.4 g of the desired product as a lower Rf mixture of isomers.

Following procedures similar to Embodiment II above: α-cyano-3-phenoxybenzyl (1R,cis)-2,2-diemthyl-3-(2-(neopentoxyimino)propyl)-cyclopropanecarboxylate, 3-phenoxybenzyl (1R,cis)-2,2-dimethyl-3-(2-(isobutoxyimino)propyl)cyclopropanecarboxylate, α-cyano-3-phenoxybenzyl (1R,cis)-2,2-dimethyl-3-(2-(cyclopropylmethoxyimino)propyl)cyclopropanecarboxylate, α-cyano-3-phenoxybenzyl (1R,cis)-2,2-dimethyl-3-(2-(cyclobutylmethoxyimino)propyl)cyclopropanecarboxylate are prepared as well as the corresponding esters in the racemic and (1R,trans) form and similar esters with other alcohols: α-ethynyl-3-phenoxybenzyl alcohol, 3,4,5,6-tetrahydrophthalimidomethyl alcohol, 2,6-dichlorobenzyl alcohol, 2-chloro-4-phenyl-2-butenl-ol and allethrolone.

Embodiment III

Pesticidal Activity

As an example, activity of the compounds of this invention with respect to insect and acarine pests was determined by using standardized test methods to test the toxicity of the compounds as follows:

Corn earworm larvae (*Heliothis zea* (Boddie) were tested by spraying a broad bean plant with dilutions of acetone solution of test compound into water containing an emulsifier. Immediately after spraying, 5 larvae were transferred to the plant and held for 44–46 hours, at which time the dead and moribund larvae were counted. The tests were conducted employing several dosage rates for each test compound.

The toxicity of the compound of the invention was compared to that of a standard pesticide (Parathion), its relative toxicity then being expressed in terms of the relationship between the amount of compound of the invention and the amount of the standard pesticide required to produce the same percentage (50) of mortality in the test insects or acarine. Assigning the standard pesticide an arbitrary rating of 100, the toxicities of the compound of the invention with that of the standard pesticide. That is to say, a test compound having a Toxicity Index of 50 would be half as active, while one having a Toxicity Index of 200 would be twice as active as the standard pesticide.

The species of Embodiment II (a) of the present invention was found to have a corn earworm toxicity value of 49 using the above procedure and the species of Embodiment II (b) was found to have a corn earworm toxicity value of 28.

I claim:

1. A compound of the formula

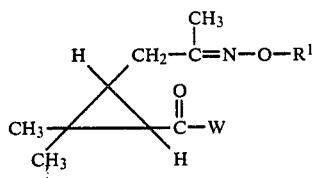

wherein $R^1$ is an alkyl group containing from 1 to 10 carbon atoms optionally substituted by one or more halogen atoms; a (cycloalkyl)-alkyl group containing from 3 to 7 ring carbon atoms, a total of from 4 to 9 carbon atoms and optionally ring-substituted by one or more halogen atoms; a cycloalkyl group containing from 3 to 7 ring carbon atoms; an alkenyl group containing from 2 to 4 carbon atoms optionally substituted by one or more halogen atoms or alkynyl group containing from 2 to 4 carbon atoms or an aryl group containing from 6 to 12 carbon atoms or an aralkyl group containing from 7 to 10 carbon atoms, each optionally ring-substituted by one or more halogen atoms;W is —OR in which R is a 3-phenoxybenzyl or α-cyano-3-phenoxybenzyl group.

2. A compound according to claim 1 wherein $R^1$ is an alkyl group containing from 1 to 5 carbon atoms.

3. A compound according to claim 2 wherein R is α-cyano-3-phenoxybenzyl.

4. A compound according to claim 3 wherein $R^1$ is isopropyl.

5. A compound according to claim 1, 2 or 3 in the (1R,cis) form.

6. A pest control composition comprises a pest controlling effective amount of a compound according to claim 1, and at least one agriculturally acceptable surface-active agent or carrier therefore.

7. A method of controlling pests which comprises applying to the pests or their habitat a pest controlling effective amount of a compound according to claim 1.

* * * * *